United States Patent
Saunders (10) Patent No.: US 8,336,665 B1
(45) Date of Patent: *Dec. 25, 2012

(54) CONCEALMENT APPARATUS FOR IGNITION INTERLOCK DEVICES

(75) Inventor: Barry Saunders, Scottsdale, AZ (US)

(73) Assignee: Capital Logistics, Inc., Carson City, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/463,559

(22) Filed: May 3, 2012

Related U.S. Application Data (63) Continuation-in-part of application No. 29/416,713, filed on Mar. 26, 2012, and a continuation-in-part of application No. 13/249,599, filed on Sep. 30, 2011.

(60) Provisional application No. 61/533,352, filed on Sep. 12, 2011.

(51) Int. Cl.
*B60K 28/00* (2006.01)

(52) U.S. Cl. .......... 180/272; 206/305; 422/84; 340/576; 73/23.3

(58) Field of Classification Search .................. 180/272; 600/532; 422/84; 340/426.11, 426.24, 576; 206/305, 306, 523, 217, 320
See application file for complete search history.

(56) References Cited

U.S. PATENT DOCUMENTS

| | | | |
|---|---|---|---|
| 5,531,225 A | 7/1996 | Nawata et al. | |
| 6,170,318 B1 | 1/2001 | Lewis | |
| 6,205,040 B1 * | 3/2001 | Teichmann | 363/57 |
| 7,279,132 B2 | 10/2007 | Sultan et al. | |
| 7,377,186 B2 | 5/2008 | Duval | |
| 7,422,723 B1 | 9/2008 | Betsill | |
| 7,451,852 B2 | 11/2008 | Stewart et al. | |
| 7,736,903 B2 | 6/2010 | Lambert et al. | |
| 2005/0009195 A1 * | 1/2005 | Wang | 436/132 |
| 2006/0016278 A1 | 1/2006 | Duval | |
| 2006/0033628 A1 | 2/2006 | Duval | |
| 2006/0206034 A1 * | 9/2006 | Stock et al. | 600/532 |
| 2006/0217625 A1 * | 9/2006 | Forrester | 600/532 |
| 2006/0274493 A1 * | 12/2006 | Richardson et al. | 361/683 |
| 2010/0012417 A1 * | 1/2010 | Walter et al. | 180/272 |
| 2010/0063408 A1 * | 3/2010 | Nothacker et al. | 600/532 |
| 2010/0269566 A1 | 10/2010 | Carroll | |
| 2011/0050407 A1 | 3/2011 | Schoenfeld | |
| 2011/0079073 A1 * | 4/2011 | Keays | 73/23.3 |
| 2012/0031166 A1 * | 2/2012 | Lopez et al. | 73/23.3 |
| 2012/0048753 A1 * | 3/2012 | Johnson-Griggs | 206/305 |
| 2012/0075094 A1 * | 3/2012 | Keays | 340/539.12 |

OTHER PUBLICATIONS

Breathalyzer / Ignition Interlock Device Camouflage! : Retrieved from: http://cgi.ebay.com/Breathalyzer-Ignition-Interlock-Device-Camouflage-1320672729463, Jun. 29, 2011.

* cited by examiner

*Primary Examiner* — Ruth Ilan
(74) *Attorney, Agent, or Firm* — Myers Bigel Sibley & Sajovec, P.A.

(57) ABSTRACT

A concealment apparatus for ignition interlock devices includes a container that has a top, a bottom, and at least one side wall separating the top and the bottom. The at least one sidewall includes a screen opening for viewing at least a screen of an ignition interlock device. The container can resemble a beverage container, such as a mug, a tumbler, a can, a sports bottle, or a thermos. An ignition interlock concealment system includes a concealment apparatus and an ignition interlock device contained therein.

16 Claims, 11 Drawing Sheets

CONCEALMENT APPARATUS FOR IGNITION INTERLOCK DEVICES

CROSS-REFERENCE TO RELATED APPLICATIONS

This application is a Continuation in part of the earlier U.S. Design patent application entitled "CONCEALMENT APPARATUS FOR IGNITION INTERLOCK DEVICES", Ser. No. 29/416,713, filed Mar. 26, 2011, now pending. This application is also a Continuation in part of the earlier U.S. Utility patent application entitled "CONCEALMENT APPARATUS FOR IGNITION INTERLOCK DEVICES", Ser. No. 13/249,599, filed Sep. 30, 2011, now pending, which claims the benefit of the provisional application entitled "CONCEALMENT APPARATUS FOR IGNITION INTERLOCK DEVICES", Ser. No. 61/533,352, filed Sep. 12, 2011. The entire disclosures of the foregoing are hereby incorporated entirely herein by reference.

BACKGROUND

1. Technical Field

This document relates to a concealment apparatus for ignition interlock devices.

2. Background

An ignition interlock device or breath alcohol ignition interlock device ("IID") is a mechanism, like a breathalyzer. Usually, an IID system is installed to a motor vehicle's dashboard. There is no universal clip for installation so often they are attached with adhesive, hook and loop fasteners, or screws, all of which can modify and "damage" the dashboard.

Before the vehicle's motor can be started, the driver first must exhale into the device. If the resultant breath-alcohol concentration analyzed result is greater than the programmed blood alcohol concentration, the device prevents the engine from being started. At random times after the engine has been started, the IID will require another breath sample. The purpose of this is to prevent a friend from breathing into the device, enabling the intoxicated person to get behind the wheel and drive away. If the breath sample isn't provided, or the sample exceeds the ignition interlock's preset blood alcohol level, the device will log the event, warn the driver and then start up an alarm (e.g., lights flashing, horn honking, etc.) until the ignition is turned off, or a clean breath sample has been provided.

In the end, people do not like having IID's installed in their cars because of the installation modifications that are required to their dashboards. They are also embarrassed by them. IIDs draw attention to themselves by, in some cases, making a car's horn honk or flash lights, but certainly when a person has to use them (blow into them, etc.).

SUMMARY

Aspects of this document relate to a concealment apparatus for ignition interlock devices and concealed ignition interlock devices. These aspects may comprise, and implementations may include, one or more or all of the components and steps set forth in the appended CLAIMS, which are hereby incorporated by reference.

In one aspect, a concealment apparatus for ignition interlock devices is disclosed. The concealment apparatus may include a container that has a top, a bottom, and at least one side wall separating the top and the bottom. The at least one sidewall includes a screen opening for at least viewing a screen of the ignition interlock device.

Particular implementations may include one or more or all of the following.

The container may be opaque or colored. The top of the container may include a through hole for one of a straw member and a mouth piece of the ignition interlock device. The bottom of the container may include a through hole for an electrical cord of the ignition interlock device. The at least one side wall of the container may include a through hole for an electrical cord of the ignition interlock device, at least one opening for at least one speaker of the ignition interlock device, and/or one of at least one opening, at least one push button, and at least one push tab for at least one input member of the ignition interlock device.

The screen opening may be one of a window and a door. The window may be one of an open window and a closed window with a clear pane. The door may be one of a sliding door and a hinged door.

The container may resemble a beverage container, such as one of a mug, a tumbler, a can, a sports bottle, and a thermos.

Resembling a mug, the container may further include a handle. The top may include a removable lid with a through hole, wherein the at least one side wall further comprises at least one opening for at least one speaker of the ignition interlock device, and wherein the handle comprises a through hole for an electrical cord of the ignition interlock device. The through hole for an electrical cord may be located in a bottom of the handle. The screen opening may be one of a window and a door. The window may be one of an open window and a closed window with a clear pane. The door may be one of a sliding door and a hinged door. The handle may further include an actuator (e.g., a trigger) that corresponds to at least one input member of the ignition interlock device. The actuator may be located in a top of the handle.

In another aspect, an ignition interlock concealment system is disclosed. The ignition interlock concealment system may include a concealment apparatus as previously described and an ignition interlock device contained therein.

In still another aspect, an ignition interlock device is disclosed. The ignition interlock device may include a housing resembling a beverage container. The housing may include a top, a bottom, and at least one side wall separating the top and the bottom, the at least one sidewall comprising a screen.

Particular implementations may include one or more or all of the following.

The housing may be opaque or colored. The housing may resemble one of a mug, a tumbler, a can, a sports bottle, and a thermos. The at least one side wall may further include a port for an electrical cord, at least one opening for at least one speaker, at least one input member, or any combination thereof.

The foregoing and other aspects and implementations of a concealment apparatus, ignition interlock concealment system, and an ignition interlock device may have one or more or all of the following advantages, as well as other benefits discussed elsewhere in this document.

Implementations allow IIDs to be discreet and "camouflaged", while still maintaining the functionality of the IID without anyone knowing what it really is. Implementations simply look as if they were an ordinary, everyday item that you would actually have in your car, like a mug, a cup or tumbler, a sports bottle, a can, a thermos, and any other similar item that could be placed in a cup holder of a car. Furthermore, dashboards do not have to be modified to hold an IID. Implementations can be placed in standard vehicle cup holders.

The foregoing and other aspects, features, and advantages will be apparent to those of ordinary skill in the art from the DESCRIPTION and DRAWINGS, and from the CLAIMS.

BRIEF DESCRIPTION OF DRAWINGS

Implementations will hereinafter be described in conjunction with the appended DRAWINGS (which are not necessarily to scale), where like designations denote like elements, and.

DESCRIPTION

This document features concealment apparatus implementations for ignition interlock devices. There are many features of concealment apparatus implementations disclosed herein, of which one, a plurality, or all features or steps may be used in any particular implementation.

In the following description, reference is made to the accompanying DRAWINGS which form a part hereof, and which show by way of illustration possible implementations. It is to be understood that other implementations may be utilized, and structural, as well as procedural, changes may be made without departing from the scope of this document. As a matter of convenience, various components will be described using exemplary materials, sizes, shapes, dimensions, and the like. However, this document is not limited to the stated examples and other configurations are possible and within the teachings of the present disclosure.

Apparatus

Turning to FIGS. 1-14 generally and for the exemplary purposes of this disclosure, there are a variety of concealment apparatus implementations for disguising ignition interlock devices while still allowing them to function.

A concealment apparatus includes a container that is meant to resemble a beverage container (a cup/tumbler or bottle or can or mug or thermos, etc.) so that it looks like all that is in a person's car is a beverage container for example and not an IID. In general, a concealment apparatus may be opaque or colored to provide complete concealment.

In specific implementations, a screen opening may be included on the opaque concealment apparatus so that the screen of the IID can be seen. In specific implementations, the screen opening could be large enough to accommodate an IID with a mouthpiece or breath tube that extends out orthogonally or horizontally from the IID above the screen (as opposed to IIDs that have breath tubes that extend out at an angle or vertically from the top corner or the top of the IID, respectively). In specific implementations, there could also be an opening (e.g., window, door, etc.) for a camera installed on an IID. The screen opening may be or include a window or a door. The window may be an open window or a closed window with a clear pane. The door may be a sliding door or a hinged door.

In specific implementations, there are also various other openings or buttons or tabs in the concealment apparatus so that any buttons, triggers, etc. on the ignition interlock device can be accessed and engaged/pushed by a user when the IID is installed inside the concealment apparatus. In specific implementations, there are also openings so that the speaker (s) of the IID can be heard (could be in the form of parallel slots or a plurality of small closely spaced holes for example, or just openings or holes that correspond to the size of the speakers).

In specific implementations, there is a hole at the bottom and/or a lower side of the concealment apparatus for the electrical cable of the IID to extend through. In specific implementations, there is also a hole in the top of the concealment apparatus (e.g., the lid) and/or an upper side of the concealment apparatus for the mouthpiece or breath tube of the IID.

In specific implementations, an integral and molded internal cavity or partial cavity is part of the concealment apparatus that corresponds to the shape or partial shape of the IID, so that the IID can be removably retained inside the concealment apparatus and not move or rotate. In specific implementations, a removable sleeve or sleeve parts (e.g., sleeve halves) are insertable inside the concealment apparatus to form a cavity or partial cavity corresponding to the shape or partial shape of the IID, so that the IID can be removably retained inside the concealment apparatus and not move or rotate. In specific implementations, a U-shaped hanger member is part of the concealment apparatus that is configured to removably receive a corresponding cylindrical member of the IID so that the IID is suspended and held inside the concealment apparatus and will not move or rotate.

System

Turning to FIGS. 6A-14 generally and for the exemplary purposes of this disclosure, there are a variety of ignition interlock concealment system implementations for disguising IIDs while still allowing them to function. An ignition interlock concealment system may generally include a concealment apparatus as described previously and an IID installed/contained therein. All components and features of the IID are accessible and able to be engaged or viewed or heard through corresponding components and features of the concealment apparatus. Again, the concealment apparatus is meant to resemble a beverage container (a cup/tumbler or sports bottle or can or mug or thermos, etc.) so that it looks like all that is in a person's car is a beverage container for example and not an IID. In specific implementations, straws can be attached to the end of the mouth piece or breath tube of the IID.

IID

Figure 17:
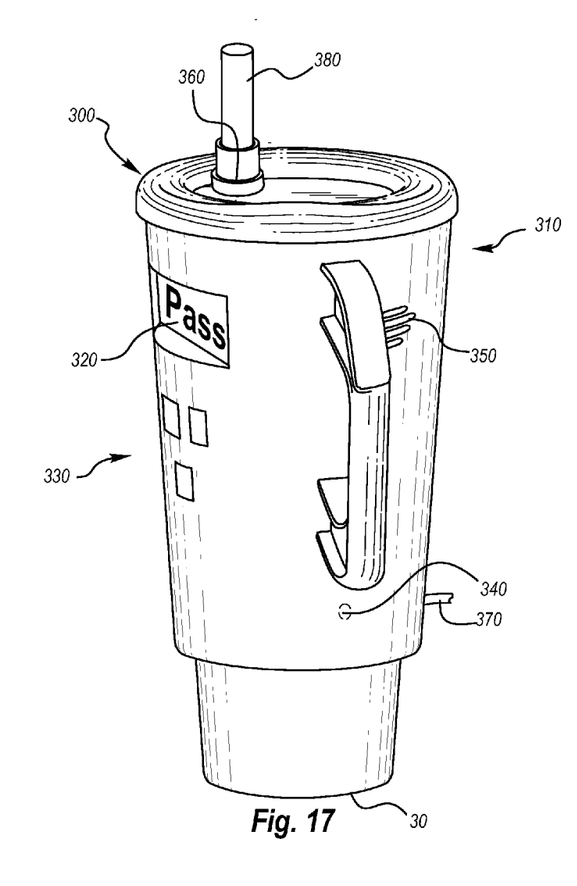
FIG. 17 is even an ignition interlock device.
Figure 18:
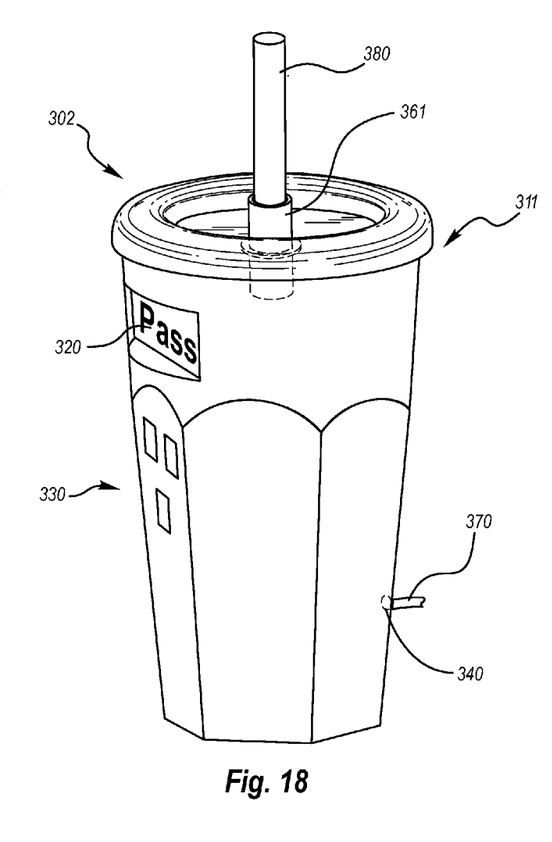
FIG. 18 is another implementation of an ignition interlock device.

Turning to FIGS. 17-18 generally and for the exemplary purposes of this disclosure, there are a variety of IID implementations for disguising IIDs while still allowing them to function. An IID may generally include a housing resembling a beverage container. The housing may include a top, a bottom, and at least one side wall separating the top and the bottom, the at least one sidewall comprising a screen. The housing may be opaque or colored. The housing may resemble a mug, a tumbler, a can, a sports bottle, or a thermos. The at least one side wall may further include a port for an electrical cord, at least one opening for at least one speaker, at least one input member, or any combination thereof. Again, the IID is meant to resemble a beverage container (a cup/tumbler or sports bottle or can or mug or thermos, etc.) so that it looks like all that is in a person's car is a beverage container for example and not an IID. In specific implementations, straws can be attached to the end of the mouth piece or breath tube of the IID.

Other and Specific Implementations

As described previously, there are many implementations of a concealment apparatus and an ignition interlock concealment system.

For the exemplary purposes of this disclosure and referring to FIGS. 1-4 and 6A and 7, concealment apparatus 1 and ignition interlock concealment system 10 are depicted. Concealment apparatus 1 includes a container that resembles a mug. The mug container is opaque or colored to conceal an enclosed IID 140.

The mug container has a top that is a removable lid 20 with a through hole 22 for receiving there through a mouthpiece 148 (or straw attached to the mouthpiece 148) of an IID 140 contained inside apparatus 1. A bottom 30 has a through hole 32 for receiving there through an electrical cord 146 of an IID 140 contained inside apparatus 1.

At least one side wall 40 separates the top 20 and the bottom 30. The sidewall 40 includes an open window 42 for viewing a screen 142 of the contained IID 140. A lower part of the sidewall 40 also has a through hole 44 for receiving there through an electrical cord 146 of an IID 140 contained inside apparatus 1. The sidewall 40 also includes at least one opening for at least one speaker of an IID 140 contained inside apparatus 1. In particular, sidewall 40 includes opposing openings 46 and 48 (which are each formed of slots) that correspond to speakers of IID 140 contained inside apparatus 1. Side wall 40 also includes at least one opening, at least one push button, or at least one push tab that corresponds to at least one input member of the IID 140. For example, IID 140 has a depressible trigger 150 on a backside that a user needs to engage during operation of IID 140. Side wall 40 may include a push tab 50 that corresponds to the trigger 150 when IID 140 is contained inside apparatus 1. Push tab 50 can be integral to side wall 40 and be formed of a U-shaped slot through the side wall 40. The back side of tab 50 can have an extension member that extends to the trigger 150 so that when tab 50 is depressed by a user, the extension member depresses the trigger 150.

Figure 7:
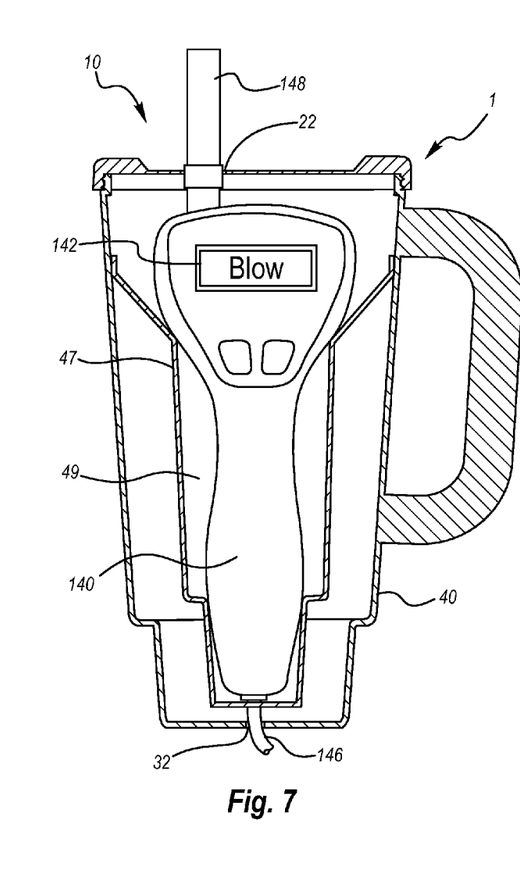
FIG. 7 is a cross-sectional view of the ignition interlock concealment system of FIG. 6A taken along line 7-7.

An internal sidewall 47 is provided that defines a cavity 49. Cavity 49 corresponds to the shape or partial shape of IID 140, so that IID 140 can be removably supported and retained in cavity 49 inside the concealment apparatus 1 and not move or rotate.

Figure 1:
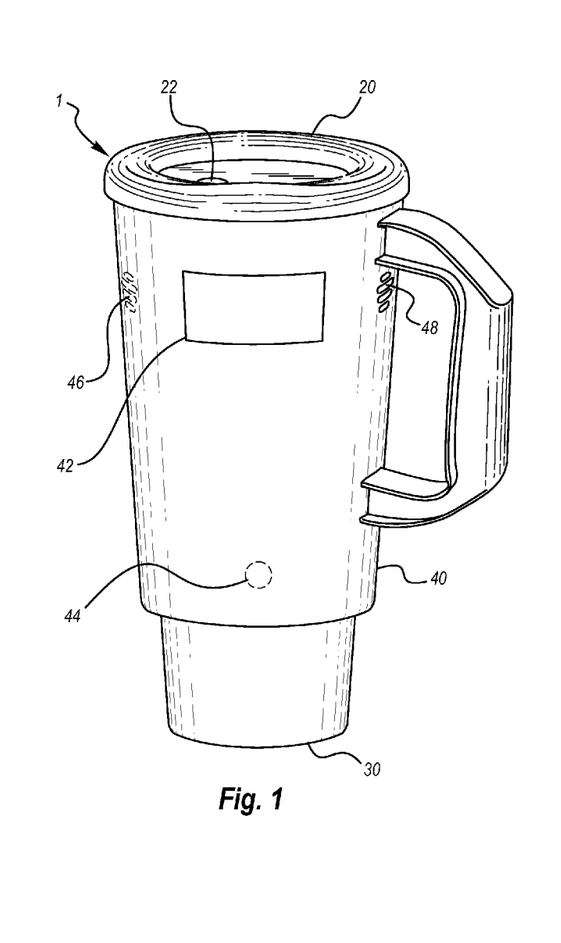
FIG. 1 is a top, front perspective view of an implementation of a concealment apparatus for ignition interlock devices.
Figure 2:
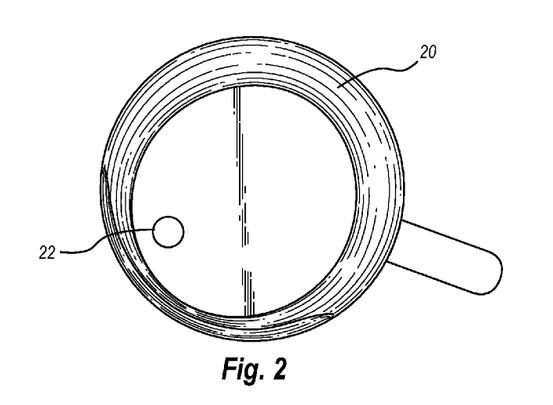
FIG. 2 is a top view of the concealment apparatus of FIG. 1.
Figure 3:
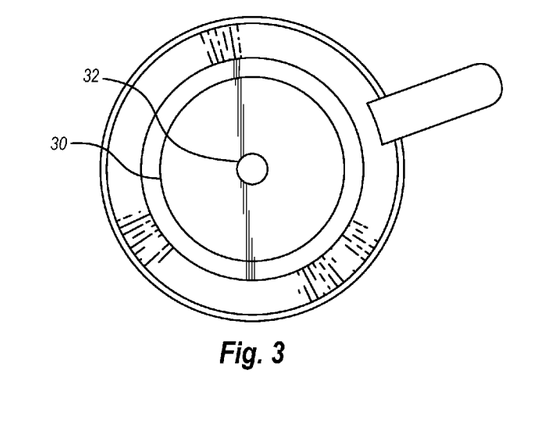
FIG. 3 is a bottom view of the concealment apparatus of FIG. 1.
Figure 4:
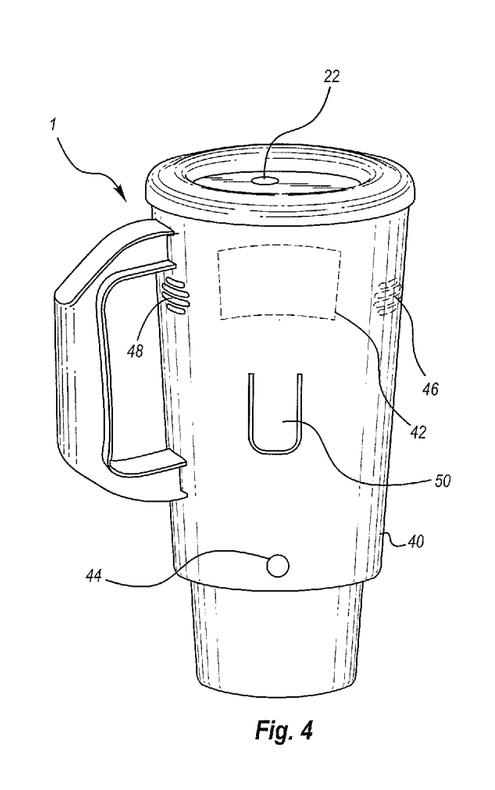
FIG. 4 is a top, back perspective view of the concealment apparatus of FIG. 1.
Figure 5:
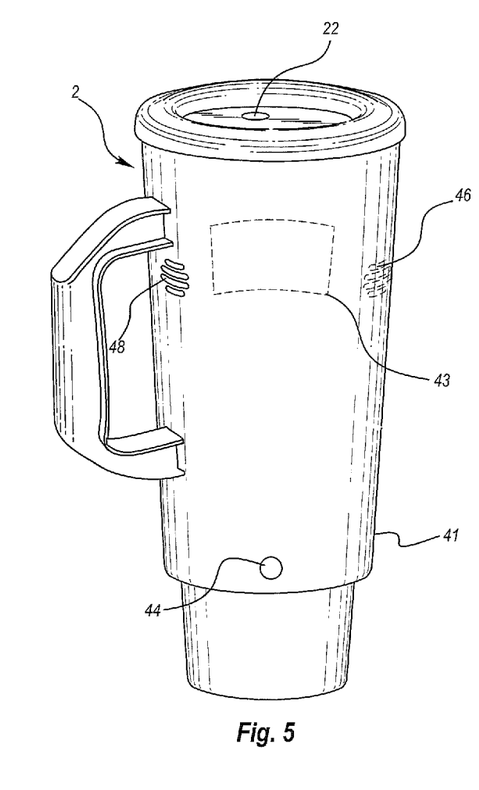
FIG. 5 is a top, back perspective view of another implementation of a concealment apparatus.
Figure 6A:
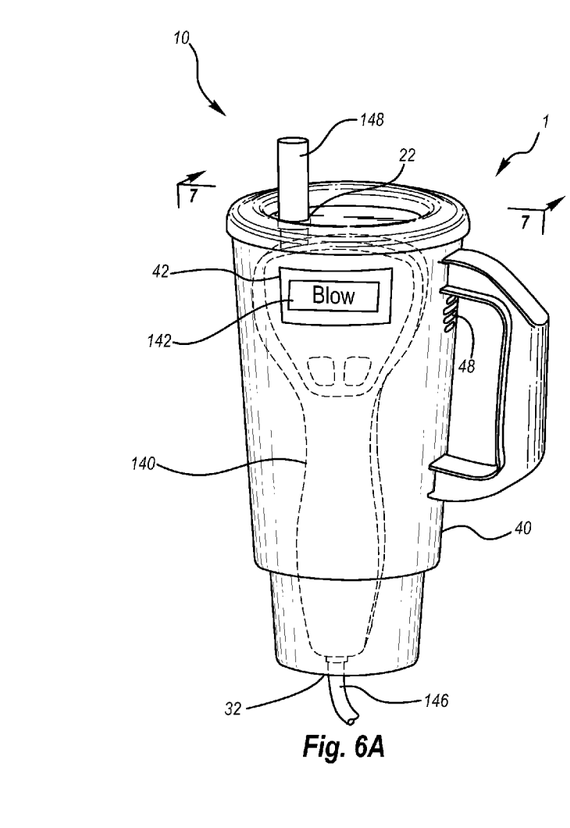
FIG. 6A is implementation of an ignition interlock concealment system including the concealment apparatus of FIG. 4 and an ignition interlock device.
Figure 6B:
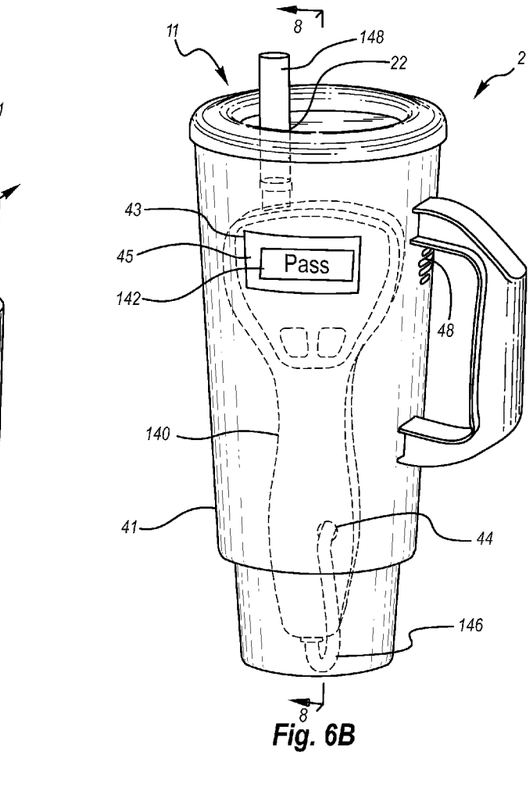
FIG. 6B is another implementation of an ignition interlock concealment system including the concealment apparatus of FIG. 5 and an ignition interlock device.
Figure 8:
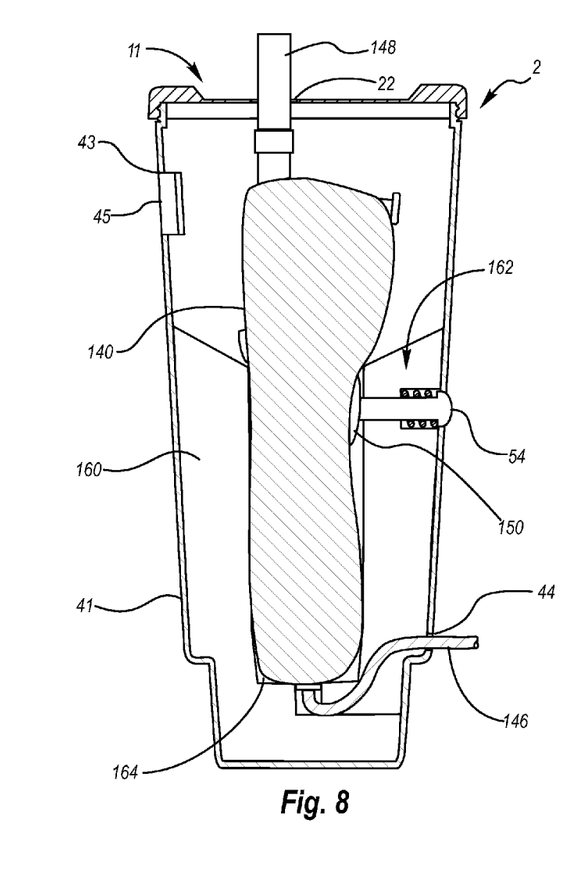
FIG. 8 is a cross-sectional view of the ignition interlock concealment system of FIG. 6B taken along line 8-8.

For the exemplary purposes of this disclosure and referring to FIGS. 5 and 6B and 8, concealment apparatus 2 and ignition interlock concealment system 11 are depicted. Concealment apparatus 2 and ignition interlock concealment system 11 are similar to concealment apparatus 1 and ignition interlock concealment system 10 as previously described, the principal differences being a larger container, push button 54, window 43, and sleeve 160.

Concealment apparatus 2 includes a container that resembles a mug. The mug container is opaque or colored to conceal an enclosed IID 140.

The mug container has a top that is a removable lid 20 with a through hole 22 for receiving there through a mouthpiece 148 (or straw attached to the mouthpiece 148) of an IID 140 contained inside apparatus 2. A bottom 30 has a through hole 32 for receiving there through an electrical cord 146 of an IID 140 contained inside apparatus 2.

At least one side wall 41 separates the top 20 and the bottom 30. The sidewall 41 includes an closed window 43 for viewing a screen 142 of the contained IID 140. The window 43 has a clear pane 45 formed of an appropriate material. A lower part of the sidewall 41 also has a through hole 44 for receiving there through an electrical cord 146 of an IID 140 contained inside apparatus 2. The sidewall 41 also includes at least one opening for at least one speaker of an IID 140 contained inside apparatus 2. In particular, sidewall 40 includes opposing openings 46 and 48 (which are each formed of slots) that correspond to speakers of IID 140 contained inside apparatus 2. Side wall 41 also includes at least one opening, at least one push button, or at least one push tab that corresponds to at least one input member of the IID 140. For example, IID 140 has a depressible trigger 150 on a backside that a user needs to engage during operation of IID 140. Side wall 41 may include a push button 54 that corresponds to the trigger 150 when IID 140 is contained inside apparatus 2. Push button 54 can be formed of a spring and an extension member that extends to the trigger 150 so that when button 54 is depressed by a user, the extension member depresses the trigger 150.

Removable sleeve 160 is provided that has an top opening and closed bottom/base and at least one side wall, all of which defining a cavity 164. Cavity 164 corresponds to the shape or partial shape of IID 140, so that IID 140 can be removably supported and retained in cavity 164 inside the concealment apparatus 1 and not move or rotate. Sleeve 160 can be a foam sleeve. Sleeve 160 may have a vertical through slot 162 defined through a side wall thereof. Slot 162 accommodates and makes accessible trigger 150, the extension member of push button 54, and electrical cord 146 exiting out through hole 44 in side wall 41.

Figure 9:
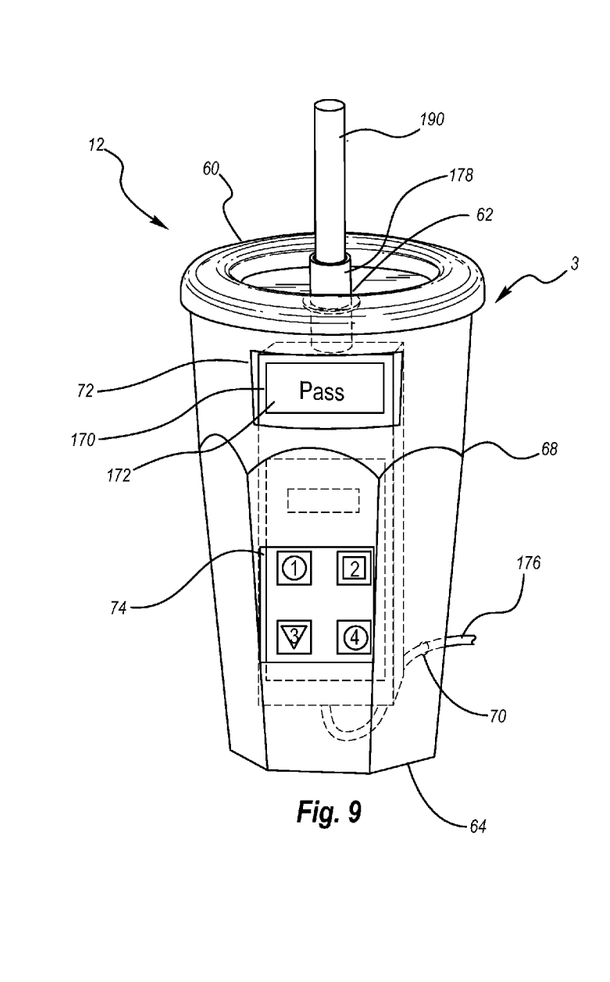
FIG. 9 is another implementation of an ignition interlock concealment system including an ignition interlock device.
Figure 10:
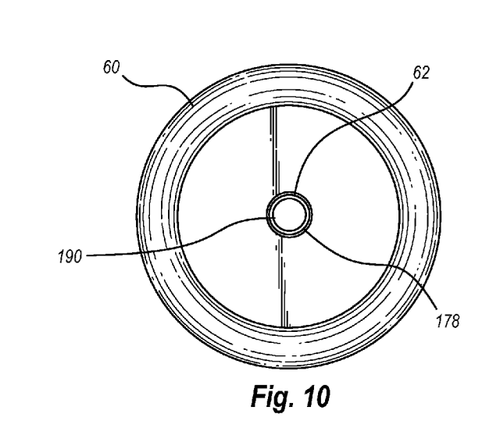
FIG. 10 is a top view of the ignition interlock concealment system of FIG. 9.
Figure 11:
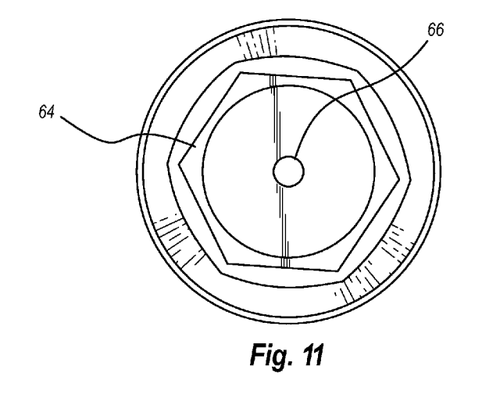
FIG. 11 is a bottom view of the ignition interlock concealment system of FIG. 9.

For the exemplary purposes of this disclosure and referring to FIGS. 9-11, concealment apparatus 3 and ignition interlock concealment system 12 are depicted. Concealment apparatus 3 and ignition interlock concealment system 12 are similar to concealment apparatus 1 and ignition interlock concealment system 10 as previously described, the principal differences being the type of container.

Concealment apparatus 3 includes a container that resembles a cup or tumbler. The tumbler container is opaque or colored to conceal an enclosed IID 170 which has a different shape and functional features than IID 140.

The tumbler container has a top that is a removable lid 60 with a through hole 62 for receiving there through a mouthpiece 178 of an IID 170 contained inside apparatus 3. A straw 190 is attached to the mouthpiece 178. A bottom 64 has a through hole 66 for receiving there through an electrical cord 176 of an IID 170 contained inside apparatus 3.

At least one side wall 68 separates the top 60 and the bottom 64. The sidewall 68 includes an open window 72 for viewing a screen 172 of the contained IID 170. A lower part of the sidewall 68 also has a through hole 70 for receiving there through an electrical cord 176 of an IID 170 contained inside apparatus 3. Side wall 68 also includes at least one opening, at least one push button, or at least one push tab that corresponds to at least one input member of the IID 170. For example, IID 170 has a depressible buttons on a front side thereof that a user needs to engage during operation of IID 170. Side wall 68 may include another open window 74 that corresponds to the buttons of IID 170 when IID 170 is contained inside apparatus 3.

While not shown, an internal sidewall or a removable sleeve that defines a cavity may be provided so that IID 170 can be removably supported and retained in inside the concealment apparatus 3 and not move or rotate.

Figure 12:
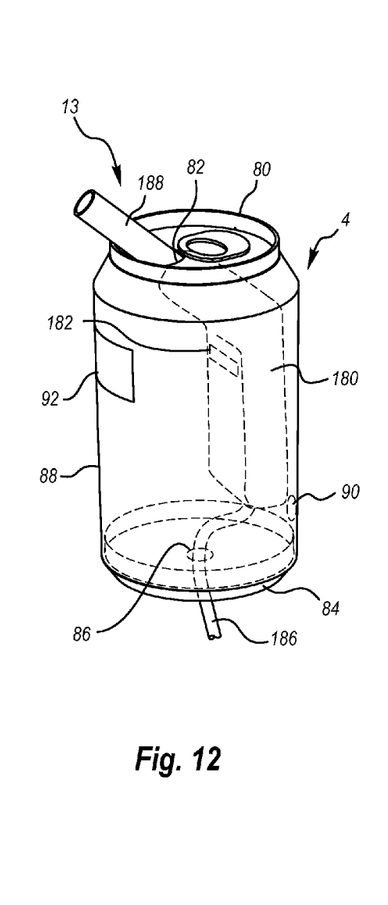
FIG. 12 is still another implementation of an ignition interlock concealment system including an ignition interlock device.

For the exemplary purposes of this disclosure and referring to FIG. 12, concealment apparatus 4 and ignition interlock concealment system 13 are depicted. Concealment apparatus 4 and ignition interlock concealment system 13 are similar to concealment apparatus 1 and ignition interlock concealment system 10 as previously described, the principal differences being the type of container.

Concealment apparatus 4 includes a container that resembles a can. The can container is opaque or colored to conceal an enclosed IID 180 which has a different shape and functional features than IIDs 140 and 170.

The can container has a top 80 with a through hole 82 for receiving there through a mouthpiece 188 of an IID 180 contained inside apparatus 4. A bottom 44 is removable (either a screw on bottom or a slip fit bottom for example) and has a through hole 86 for receiving there through an electrical cord 186 of an IID 180 contained inside apparatus 3.

At least one side wall 88 separates the top 80 and the bottom 84. The sidewall 88 includes an open or closed window 92 for viewing a screen 182 of the contained IID 180. A lower part of the sidewall 88 also has a through hole 90 for receiving there through an electrical cord 186 of an IID 180 contained inside apparatus 4. Though not shown, side wall 88 may also includes at least one opening, at least one push button, or at least one push tab that corresponds to at least one input member of the IID 180, as well as an internal sidewall or a removable sleeve that defines a cavity so that IID 180 can be removably supported and retained in inside the concealment apparatus 4 and not move or rotate.

Figure 13:
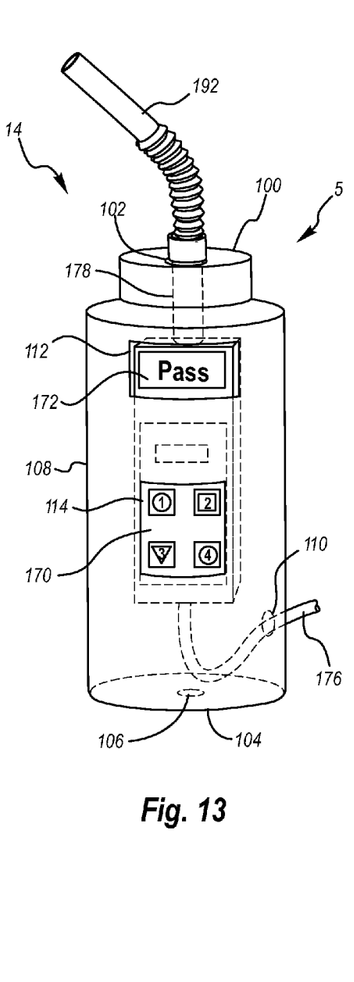
FIG. 13 is yet another implementation of an ignition interlock concealment system including an ignition interlock device.

For the exemplary purposes of this disclosure and referring to FIG. 13, concealment apparatus 5 and ignition interlock concealment system 14 are depicted. Concealment apparatus 5 and ignition interlock concealment system 14 are similar to concealment apparatus 1 and ignition interlock concealment system 10 as previously described, the principal differences being the type of container.

Concealment apparatus 5 includes a container that resembles a sports bottle. The bottle container is opaque or colored to conceal an enclosed IID 170.

The tumbler container has a top that is a removable screw-on lid 100 with a through hole 102 for receiving there through a mouthpiece 178 of an IID 170 contained inside apparatus 5. A straw 192 is attached to the mouthpiece 178. A bottom 104 has a through hole 106 for receiving there through an electrical cord 176 of an IID 170 contained inside apparatus 5.

At least one side wall 108 separates the top 100 and the bottom 104. The sidewall 108 includes an open or closed window 112 for viewing a screen 172 of the contained IID 170. A lower part of the sidewall 108 also has a through hole 110 for receiving there through an electrical cord 176 of an IID 170 contained inside apparatus 5. Side wall 108 also includes at least one opening, at least one push button, or at least one push tab that corresponds to at least one input member of the IID 170. For example, IID 170 has a depressible buttons on a front side thereof that a user needs to engage during operation of IID 170. Side wall 108 may include another open window 114 that corresponds to the buttons of IID 170 when IID 170 is contained inside apparatus 5.

While not shown, an internal sidewall or a removable sleeve that defines a cavity may be provided so that IID 170 can be removably supported and retained in inside the concealment apparatus 5 and not move or rotate.

Figure 14:
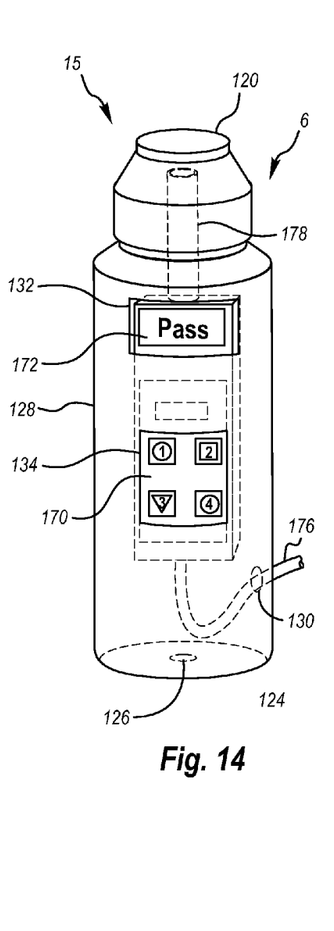
FIG. 14 is even another implementation of an ignition interlock concealment system including an ignition interlock device.

For the exemplary purposes of this disclosure and referring to FIG. 14, concealment apparatus 6 and ignition interlock concealment system 15 are depicted. Concealment apparatus 6 and ignition interlock concealment system 15 are similar to concealment apparatus 1 and ignition interlock concealment system 10 as previously described, the principal differences being the type of container.

Concealment apparatus 6 includes a container that resembles a thermos. The thermos container is opaque or colored to conceal an enclosed IID 170.

The thermos container has a top that is a removable screw-on lid 120. Mouthpiece 178 of an IID 170 contained inside lid 120 and is accessible when lid 120 is unscrewed. A bottom 124 has a through hole 126 for receiving there through an electrical cord 176 of an IID 170 contained inside apparatus 6.

At least one side wall 128 separates the top 120 and the bottom 126. The sidewall 128 includes an open window 132 for viewing a screen 172 of the contained IID 170. A lower part of the sidewall 128 also has a through hole 130 for receiving there through an electrical cord 176 of an IID 170 contained inside apparatus 6. Side wall 128 also includes at least one opening, at least one push button, or at least one push tab that corresponds to at least one input member of the IID 170. For example, IID 170 has a depressible buttons on a front side thereof that a user needs to engage during operation of IID 170. Side wall 128 may include another open window 134 that corresponds to the buttons of IID 170 when IID 170 is contained inside apparatus 6.

While not shown, an internal sidewall or a removable sleeve that defines a cavity may be provided so that IID 170 can be removably supported and retained in inside the concealment apparatus 6 and not move or rotate.

For the exemplary purposes of this disclosure, instead of being two separate devices (a concealment apparatus and an IID) that form a concealment system as described in previous implementations, they could be one in the same device. That is, the actual housing of the IID itself could be formed into the shape of a mug, tumbler, thermos, bottle, can, etc.

For the exemplary purposes of this disclosure and referring to FIGS. 17 and 18, IIDs 300 and 302 are depicted. IIDs 300 and 302 are fully functioning IIDs with all the necessary electrical, computer, mechanical, etc. components required to analyze breath-alcohol concentration, etc. IIDs 300 and 302 are similar, except IID 300 includes a housing 310 resembling a mug, while IID 302 includes a housing 311 resembling a tumbler/cup. Each housing 310 and 311 includes a top, a bottom, and at least one side wall separating the top and the bottom, the at least one sidewall including a screen 320. The housings 310 and 311 may be opaque or colored. The at least one side wall of the housings 310 may further include a port 340 for an electrical cord 370, at least one opening 350 for at least one speaker, at least one input member 330, or any combination thereof. Also included are mouthpieces 360 and 361, and if desired to further carry out the effect of resembling a beverage container, straw members 380 may be included.

Figure 19:
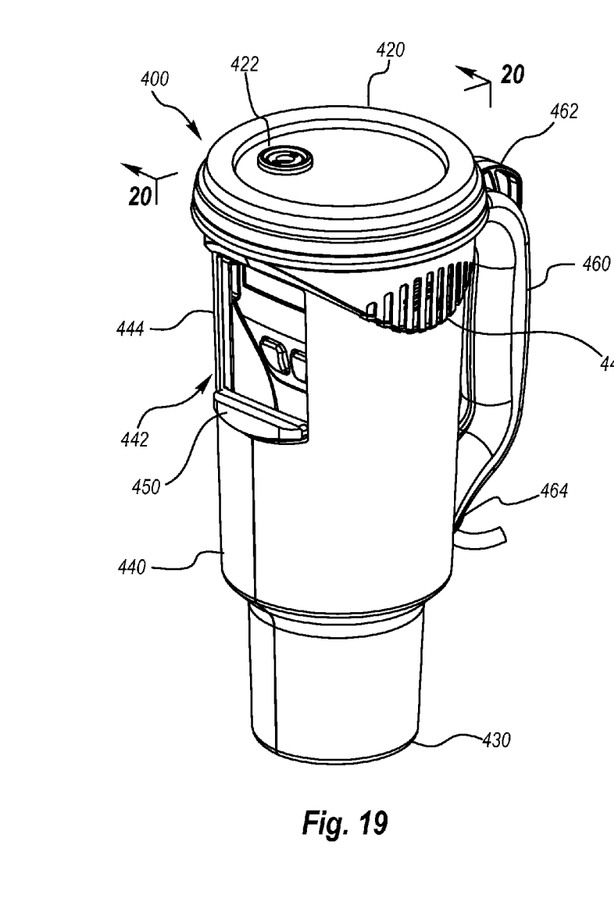
FIG. 19 is a front perspective view of another implementation of an ignition interlock concealment system including an ignition interlock device.
Figure 20:
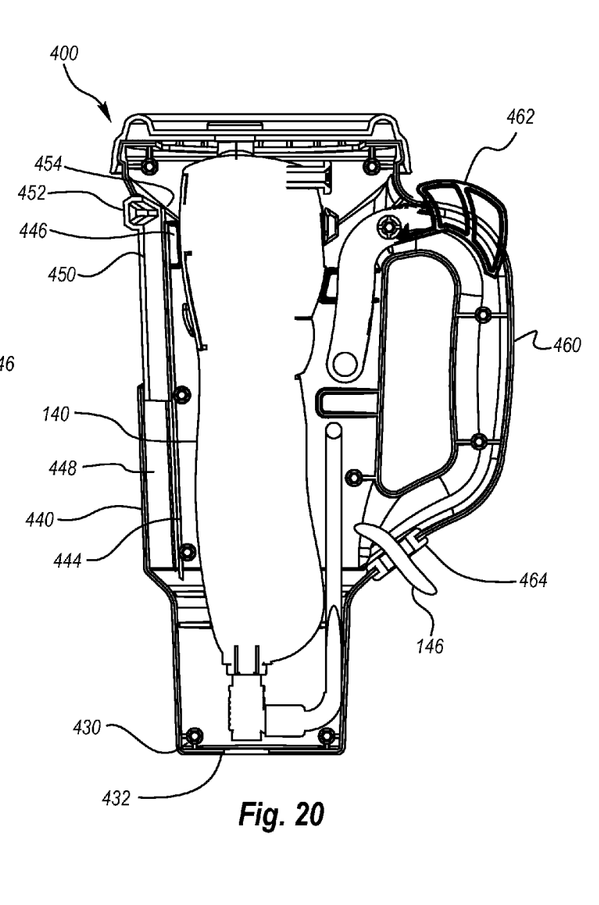
FIG. 20 is a cross-sectional view of the ignition interlock concealment system of FIG. 19 taken along line 20-20.
Figures 21, 22:
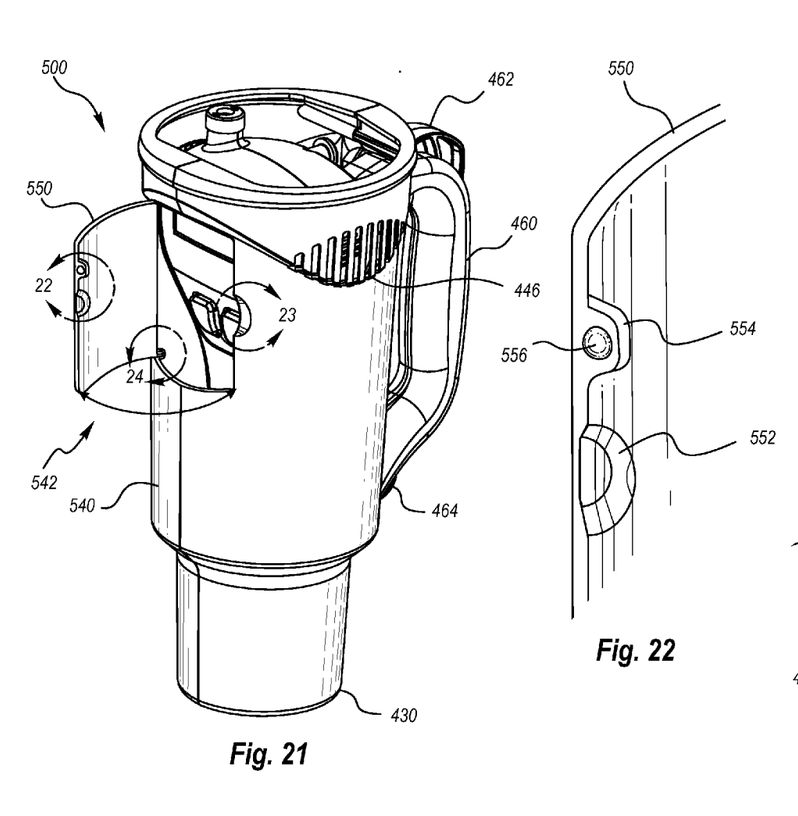
FIG. 21 is a front perspective view of another implementation of an ignition interlock concealment system including an ignition interlock device.
FIGS. 22-24 are each a portion of a view of the ignition interlock concealment system of FIG. 21 enlarged view for magnification purposes.
Figure 23:
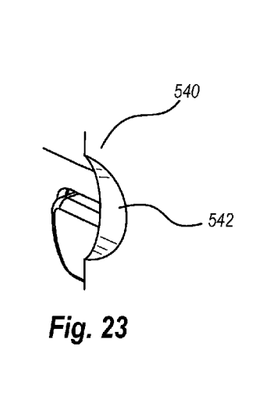
Figure 24:
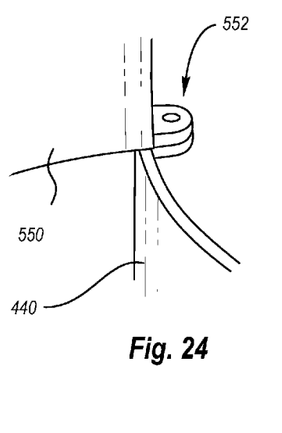

For the exemplary purposes of this disclosure and referring to FIGS. 19-20, ignition interlock concealment system 400 is depicted. Ignition interlock concealment system 400 is similar to concealment apparatus 1 and ignition interlock concealment system 10 as previously described, the principal differences being access sliding door 450, actuator 462, and grommet 464.

Ignition interlock concealment system 400 includes a concealment apparatus that includes a container that resembles a mug. The mug container may be opaque or colored to conceal an enclosed IID 140.

The mug container has a top that is a removable lid 420 with a through hole 422 for receiving there through a mouthpiece (or straw attached to the mouthpiece) of an IID 140 contained therein. A bottom 430 has a through hole 432 for receiving there through an electrical cord 146 of an IID 140.

At least one side wall 440 separates the top 420 and the bottom 430. The sidewall 440 may be formed of two casing halves coupled together, which may aid in the manufacture and assembly of the concealment apparatus. The sidewall 440 defines a screen opening 444 for viewing a screen of the contained IID 140. Interfacing with screen opening 444 is door assembly 442. Door assembly 442 includes access sliding door 450 with a handle 452 that is configured to be slid up or down by a user in an internal pocket 448 defined by sidewall 440 and track 444. Door 450 includes an internal protrusion or bump 454 that removably engages with an internal ledge 446 of track 444 to removably keep door 450 in an up, closed position.

The sidewall 440 also includes at least one opening for at least one speaker of an IID 140. In particular, sidewall 440 includes opposing openings 446 (which are each formed of slots) that correspond to speakers of IID 140 contained inside the concealment apparatus.

Resembling a mug, the concealment apparatus may further include a handle 460. Handle 460 may include a through hole for an electrical cord 146 of ignition interlock device 140. The through hole may be located in a bottom of the handle 460 and may include a grommet 464 to protect cord 146. Handle 460 may further include an actuator 462 (e.g., a trigger) that corresponds to at least one input member of the ignition interlock device 140 (IID 140 has a depressible trigger 150 on a backside that a user needs to engage during operation of IID 140). The actuator 462 may be located in a top of the handle 460 with a portion (e.g., an arm) extending into the internal cavity of the concealment apparatus to removably interface (engage and disengage) with at least one input member of the ignition interlock device 140. Actuator 462 may pivot and may have a spring that biases it in a disengaged position.

For the exemplary purposes of this disclosure and referring to FIGS. 21-24, ignition interlock concealment system 500 is depicted. Ignition interlock concealment system 500 is similar to ignition interlock concealment system 400 as previously described, the principal difference being access hinged door 550.

At least one side wall 540 separates the top (not shown) and the bottom 430. The sidewall 540 may be formed of two casing halves coupled together, which may aid in the manufacture and assembly of the concealment apparatus. The sidewall 540 defines a screen opening for viewing a screen of the contained IID 140. Interfacing with the screen opening is door assembly 542. Door assembly 542 includes access hinged door 550 that is attached at one edge thereof to a corresponding edge of the screen opening by internal hinges 552 (though external hinges may be used instead). An opposing edge of door 550 may include an arm 554 that may extend orthogonally inwardly and that defines thereon a protrusion or bump 556. As the door 550 is opened or shut, arm 554 flexes and bump 556 disengages or engages with a corresponding edge of the screen opening. That same edge of the screen opening may have defined therein a recess 542 to at least partially accommodate a user's thumb or finger so that it can be at least partially inserted therein behind door 550 when it is closed to open door 550. Optionally, the opposing edge of door 550 may further define therein a recess 552 that corresponds with recess 542 to at least partially accommodate a user's thumb or finger so that it can be at least partially inserted therein behind door 550 when it is closed to open door 550.

For the exemplary purposes of this disclosure, any aspects, features, components, and the like of any implementation described in this disclosure can be combined with any aspects, features, components, and the like of one or more or all of the other implementations.

Further implementations are within the CLAIMS.

Specifications, Materials Manufacture, Assembly

It will be understood that implementations are not limited to the specific components disclosed herein, as virtually any components consistent with the intended operation of a concealment apparatus implementation may be utilized. Accordingly, for example, although particular components and so forth, are disclosed, such components may comprise any shape, size, style, type, model, version, class, grade, measurement, concentration, material, weight, quantity, and/or the like consistent with the intended operation of a concealment apparatus implementation. Implementations are not limited to uses of any specific components, provided that the components selected are consistent with the intended operation of a concealment apparatus implementation.

Accordingly, the components defining any concealment apparatus implementation may be formed of any of many different types of materials or combinations thereof that can readily be formed into shaped objects provided that the components selected are consistent with the intended operation of a concealment apparatus implementation. For example, the components may be formed of: rubbers (synthetic and/or natural) and/or other like materials; glasses (such as fiberglass), carbon-fiber, aramid-fiber, any combination thereof, and/or other like materials; polymers such as thermoplastics (such as ABS, Fluoropolymers, Polyacetal, Polyamide; Polycarbonate, Polyethylene, Polysulfone, and/or the like), thermosets (such as Epoxy, Phenolic Resin, Polyimide, Polyurethane, Silicone, and/or the like), any combination thereof, and/or other like materials; foams formed of polymers and/or other like materials; composites and/or other like materials; metals, such as zinc, magnesium, titanium, copper, iron, steel, carbon steel, alloy steel, tool steel, stainless steel, spring steel, aluminum, any combination thereof, and/or other like materials; alloys, such as aluminum alloy, titanium alloy, magnesium alloy, copper alloy, any combination thereof, and/or other like materials; any other suitable material; and/or any combination thereof.

For the exemplary purposes of this disclosure, concealment apparatus implementations may be made of any material such as polymers, metals, composites, ceramics, and/or the like. The material(s) may be picked so as to make the concealment apparatus have any desirable attribute such as strength, light weight, opaqueness, durability, aesthetic appeal, the ability to easily grip and/or hold the concealment apparatus, and so forth.

Various concealment apparatus implementations may be manufactured using conventional procedures as added to and improved upon through the procedures described here. Some components defining concealment apparatus implementations may be manufactured simultaneously and integrally joined with one another, while other components may be purchased pre-manufactured or manufactured separately and then assembled with the integral components.

Manufacture of these components separately or simultaneously may involve extrusion, pultrusion, vacuum forming, injection molding, blow molding, resin transfer molding, casting, forging, cold rolling, milling, drilling, reaming, turning, grinding, stamping, cutting, bending, welding, soldering, hardening, riveting, punching, plating, and/or the like. If any of the components are manufactured separately, they may then be coupled with one another in any manner, such as with adhesive, a weld, a fastener, wiring, any combination thereof, and/or the like for example, depending on, among other considerations, the particular material forming the components.

It will be understood that the assembly of concealment apparatus implementations are not limited to the specific order of steps as disclosed in this document. Any steps or sequence of steps of the assembly of concealment apparatus implementations indicated herein are given as examples of possible steps or sequence of steps and not as limitations, since various assembly processes and sequences of steps may be used to assemble concealment apparatus implementations.

Use

Implementations of concealment apparatus are particularly useful in IID applications as previously explained. Implementations of concealment apparatus are particularly useful in IID applications as previously explained. Implementations allow allow IIDs to be discreet and "camouflaged", while still maintaining the functionality of the IID without anyone knowing what it really is. Implementations simply look as if they were an ordinary, everyday item that you would actually have in your car, like a mug, a cup or tumbler, a sports bottle, a can, a thermos, and any other similar item that could be placed in a cup holder of a car. However, implementations are not limited to uses relating to specific IIDs. Rather, any description relating to a particular IID is for the exemplary purposes of this disclosure, and implementations may also be used with a variety of other IIDs with similar results.

Figure 15:
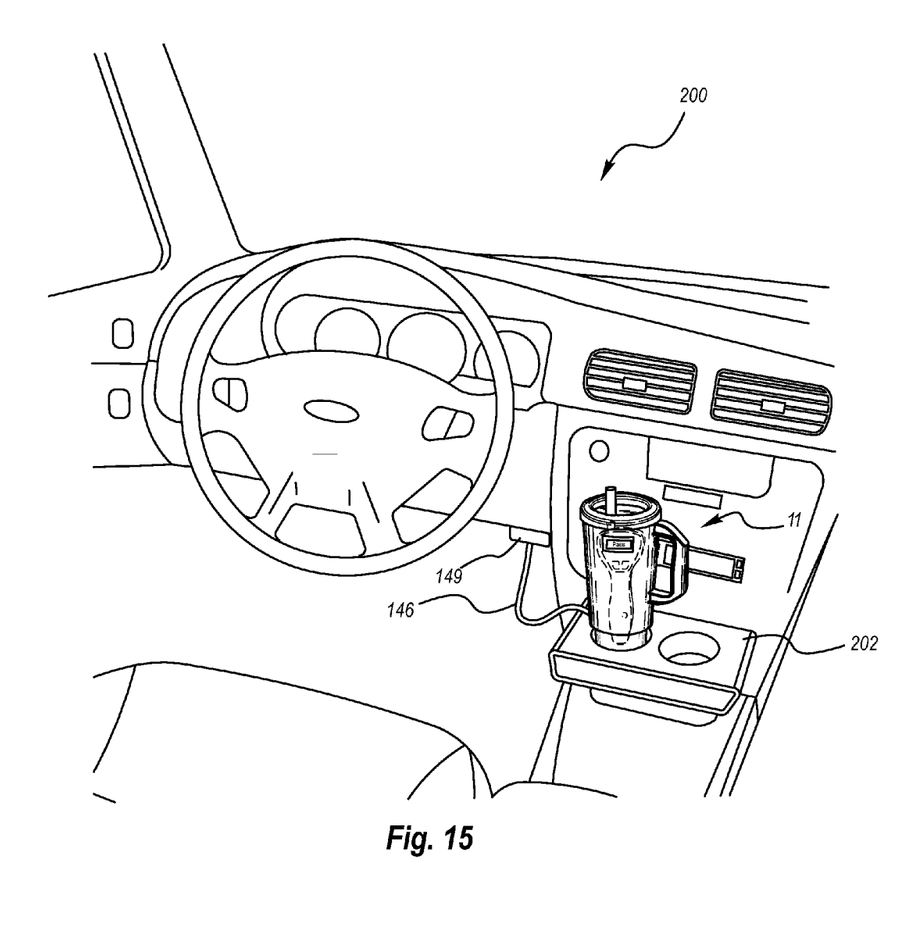
FIGS. 15-16 are perspective views of the ignition interlock concealment system of FIG. 6B in use in a vehicle with a driver.
Figure 16:
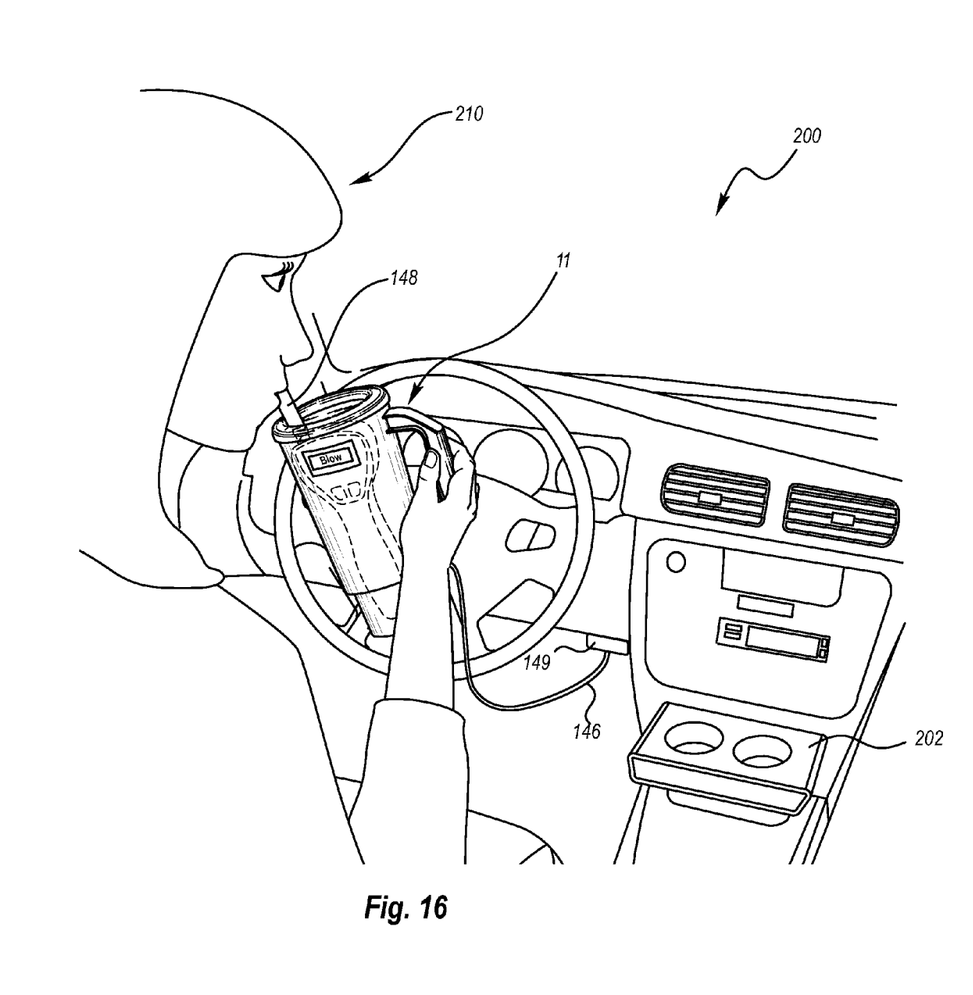

For the exemplary purposes of this disclosure and describing the use of concealment apparatus implementations further, reference is made to FIGS. 15-16. In operation, ignition interlock concealment system 11 can be placed in cup holder 202 of vehicle 200. Electrical cord 146 of IID 140 can come out the side wall 40 of apparatus 1 and extend to module 149 mounted to the underside of the dashboard for example.

Before the vehicle 200 motor can be started, the driver 210 first must exhale into IID 140 contained in apparatus 1 forming system 11. If the resultant breath-alcohol concentration analyzed result is greater than the programmed blood alcohol concentration, IID 140 prevents the engine from being started.

At random times after the engine has been started, the IID 140 will require another breath sample as depicted in FIG. 16. The purpose of this is to prevent a friend from breathing into the device, enabling the intoxicated person to get behind the wheel and drive away. If the breath sample isn't provided, or the sample exceeds the IID 140 preset blood alcohol level, IID 140 will log the event, warn the driver 210 and then start up an alarm (e.g., lights flashing, horn honking, etc.) until the ignition is turned off, or a clean breath sample has been provided.

Notwithstanding, IID 140 remains discreet and "camouflaged" in apparatus 1, while still being functional. System 11 simply looks like a mug—an ordinary, everyday item that you would actually have in your car—that could be placed in a standard cup holder 202 of a vehicle 200 without having to modify the dashboard to hold IID 140. When driver 210 blows into mouthpiece 148, it simply appears as if driver 210 is drinking from a mug.

In places where the description above refers to particular implementations, it should be readily apparent that a number of modifications may be made without departing from the spirit thereof and that these implementations may be alternatively applied. The accompanying CLAIMS are intended to cover such modifications as would fall within the true spirit and scope of the disclosure set forth in this document. The presently disclosed implementations are, therefore, to be considered in all respects as illustrative and not restrictive, the scope of the disclosure being indicated by the appended CLAIMS rather than the foregoing DESCRIPTION. All changes that come within the meaning of and range of equivalency of the CLAIMS are intended to be embraced therein.

The invention claimed is:

1. A concealment apparatus for containing an ignition interlock device comprising:
    a container that resembles a mug, comprising:
        a top comprising a removable lid with a through hole;
        a bottom; and
        at least one side wall separating the top and the bottom, wherein the at least one sidewall comprises a handle having a through hole for an electrical cord of the ignition interlock device, wherein the at least one side wall comprises at least one opening for at least one speaker of the ignition interlock device, and wherein the at least one sidewall comprises a screen opening for at least viewing a screen of the ignition interlock device.

2. The concealment apparatus of claim 1 wherein the container is opaque.

3. The concealment apparatus of claim 1 wherein the removable lid through hole is configured to receive one of a straw member and a mouth piece of the ignition interlock device.

4. The concealment apparatus of claim 1 wherein the at least one side wall further comprises a through hole for an electrical cord of the ignition interlock device.

5. The concealment apparatus of claim 1 wherein the screen opening comprises one of a window and a door.

6. The concealment apparatus of claim 5 wherein the screen opening comprises a window, and wherein the window comprises one of an open window and a closed window with a clear pane.

7. The concealment apparatus of claim 5 wherein the screen opening comprises a door, and wherein the door comprises one of a sliding door and a hinged door.

8. The concealment apparatus of claim 1 wherein the through hole for an electrical cord is located in a bottom of the handle.

9. The concealment apparatus of claim 1 wherein the screen opening comprises one of a window and a door.

10. The concealment apparatus of claim 9 wherein the screen opening comprises a window, and wherein the window comprises one of an open window and a closed window with a clear pane.

11. The concealment apparatus of claim 9 wherein the screen opening comprises a door, and wherein the door comprises one of a sliding door and a hinged door.

12. The concealment apparatus of claim 1 wherein the handle further comprises an actuator that corresponds to at least one input member of the ignition interlock device.

13. An ignition interlock concealment system comprising:
 a container comprising:
 a top;
 a bottom; and
 at least one side wall separating the top and the bottom, the at least one sidewall comprising a screen opening and a handle having a through hole for an electrical cord of an ignition interlock device contained inside the container; and
 an ignition interlock device contained inside the container so that at least a screen of the contained ignition interlock device is viewable through the screen opening.

14. The ignition interlock concealment system of claim 13, wherein one of:
 the top comprises a through hole for one of a straw member and a mouth piece of the ignition interlock device;
 the bottom comprises a through hole for an electrical cord of the ignition interlock device; and
 the at least one side wall further comprises at least one opening for at least one speaker of the ignition interlock device.

15. The ignition interlock concealment system of claim 13, the screen opening comprises one of an open window, a closed window with a clear pane, a sliding door, and a hinged door.

16. The ignition interlock concealment system of claim 13, wherein the container resembles a mug.

\* \* \* \* \*